(12) United States Patent
Nakata et al.

(10) Patent No.: US 6,488,836 B1
(45) Date of Patent: Dec. 3, 2002

(54) CO GAS SENSOR AND METHOD OF USING SAME

(75) Inventors: Toshihide Nakata, Hokkaido (JP); Hidemi Akita, Hokkaido (JP); Katsuhiko Saguchi, Hokkaido (JP); Keiji Kunimatsu, Hokkaido (JP)

(73) Assignee: Kabushikikaisha Equos Research (JP)

( * ) Notice: Subject to any disclaimer, the term of this patent is extended or adjusted under 35 U.S.C. 154(b) by 0 days.

(21) Appl. No.: 09/625,729

(22) Filed: Jul. 26, 2000

(30) Foreign Application Priority Data

Jul. 29, 1999 (JP) .......................................... 11-214498

(51) Int. Cl.[7] .......................................... G01N 27/407
(52) U.S. Cl. .................. 205/784; 204/424; 204/425; 204/426; 429/12; 429/90
(58) Field of Search ................. 204/421–429; 429/90, 12; 205/783.5, 784, 784.5, 785

(56) References Cited

U.S. PATENT DOCUMENTS

| | | | |
|---|---|---|---|
| 3,691,023 A | * | 9/1972 | Ruka et al. |
| 3,720,597 A | * | 3/1973 | Ashe et al. |
| 3,856,574 A | * | 12/1974 | Amagi et al. |
| 4,021,326 A | * | 5/1977 | Pollner et al. |
| 4,107,019 A | * | 8/1978 | Takao et al. |
| 4,283,441 A | * | 8/1981 | Haecker et al. |
| 4,729,824 A | | 3/1988 | Giner |
| 5,272,017 A | * | 12/1993 | Swathirajan et al. |
| 5,302,274 A | * | 4/1994 | Tomantschger et al. |
| 5,856,036 A | * | 1/1999 | Smotkin et al. |
| 5,939,220 A | * | 8/1999 | Gunner et al. |
| 6,063,516 A | * | 5/2000 | Grot et al. |
| 6,066,410 A | * | 5/2000 | Aver et al. |

FOREIGN PATENT DOCUMENTS

WO    WO97/40371    10/1997

* cited by examiner

Primary Examiner—T. Tung
(74) Attorney, Agent, or Firm—Lorusso & Loud

(57) ABSTRACT

A CO gas sensor is equipped with a detecting unit in which a solid electrolyte membrane is held between a detection electrode and a counter electrode, and a voltage applying unit which applies voltage between the detection electrode and the counter electrode and changes the voltage. The detection electrode includes an electrochemically active first catalyst in an electrically conductive porous body, a reaction layer having a density of 1 ng/cm$^2$–100 $\mu$g/cm$^2$ and having a thickness of 0.3 nm–15 $\mu$m, and the counter electrode includes an electrochemically active second catalyst carried on an electrically conductive porous body.

18 Claims, 13 Drawing Sheets

CO CONCENTRATION CALIBRATION CURVE

CO GAS SENSOR AND METHOD OF USING SAME

BACKGROUND OF THE INVENTION

The present invention relates to a CO gas sensor. The CO gas sensor of the present invention is suitable for detecting the concentration of a tiny amount of CO gas in an atmosphere rich in hydrogen gas and is suitably used in a fuel cell which employs a methanol-reforming gas as a fuel gas.

A novel gas sensor disclosed in the International Publication No. WO97/40371. The principle of the pulse method used in this gas sensor will be explained with reference to FIGS. 1–3. As shown in FIG. 1, this CO gas sensor has an electrolyte membrane 3 between a detection electrode 1 and a counter electrode 2. Positive voltage is applied to the detection electrode 1 by a sensor controlling unit 5. As shown in the upper part of FIG. 2, when voltage applied to the detection electrode is varied from relatively high CO oxidation potential to relatively low CO adsorption potential, a transient current (response current) flows as shown in the lower part of the same figure. This response current decreases with an increase in concentration of CO in a test gas. Then, the concentration of CO can be determined by reference to a calibration curve for the relationship between the rate of decrease of current and the CO concentration and comparing the measured rate of decrease in current with the calibration curve as shown in FIG. 3.

The present inventors have noted the following problems in the above gas sensor:

When the response current flowing between a detection electrode and a counter electrode is large, the performance of the sensor is reduced.

The sensitivity to CO gas is in need of improvement.

Insensitivity to environmental factors such as temperature and humidity is desirable; that is, a CO sensor which can measure over a wide temperature range and humidity range is needed.

A reference electrode has been used in the prior art CO sensor. However, from the viewpoint of miniaturization and weight reduction by decrease in the number of parts and, therefore, reduction in the manufacturing cost, it is desirable to omit this reference electrode.

SUMMARY OF THE INVENTION

In order to solve one or more of the aforementioned problems, the present invention provides a CO gas sensor including a detecting unit in which a solid electrolyte membrane is held between a detection electrode and a counter electrode and a voltage source which applies voltage between the detection electrode and the counter electrode and which varies the voltage. The detection electrode includes a first electrochemically active catalyst carried on an electrically conductive porous body and a reaction layer formed thereon having a density of 1 $ng/cm^2$–100 $\mu g/cm^2$ and a thickness of 0.3 nm–15 $\mu m$. The counter electrode includes a second electrochemically active catalyst carried on an electrically conducive porous body. In the CO gas sensor thus constructed, the current flowing between the detection electrode and the counter electrode can be minimized. Accordingly, elevated temperature in the sensor and drying of the electrolyte membrane can be prevented, leading to a long life for the sensor. Since the current can be small, the sensitivity to CO gas is improved.

In addition, the temperature range and humidity range over which the CO gas sensor can be effectively operated are widened.

Further, stable measurement of CO gas becomes possible even without a reference electrode.

BRIEF DESCRIPTION OF THE DRAWINGS

These and other objects and technical advantages of the present invention will be readily apparent from the following description of the preferred embodiments of the invention in conjunction with the accompanying drawings, in which.

DESCRIPTION OF THE PREFERRED EMBODIMENTS

Figure 4:
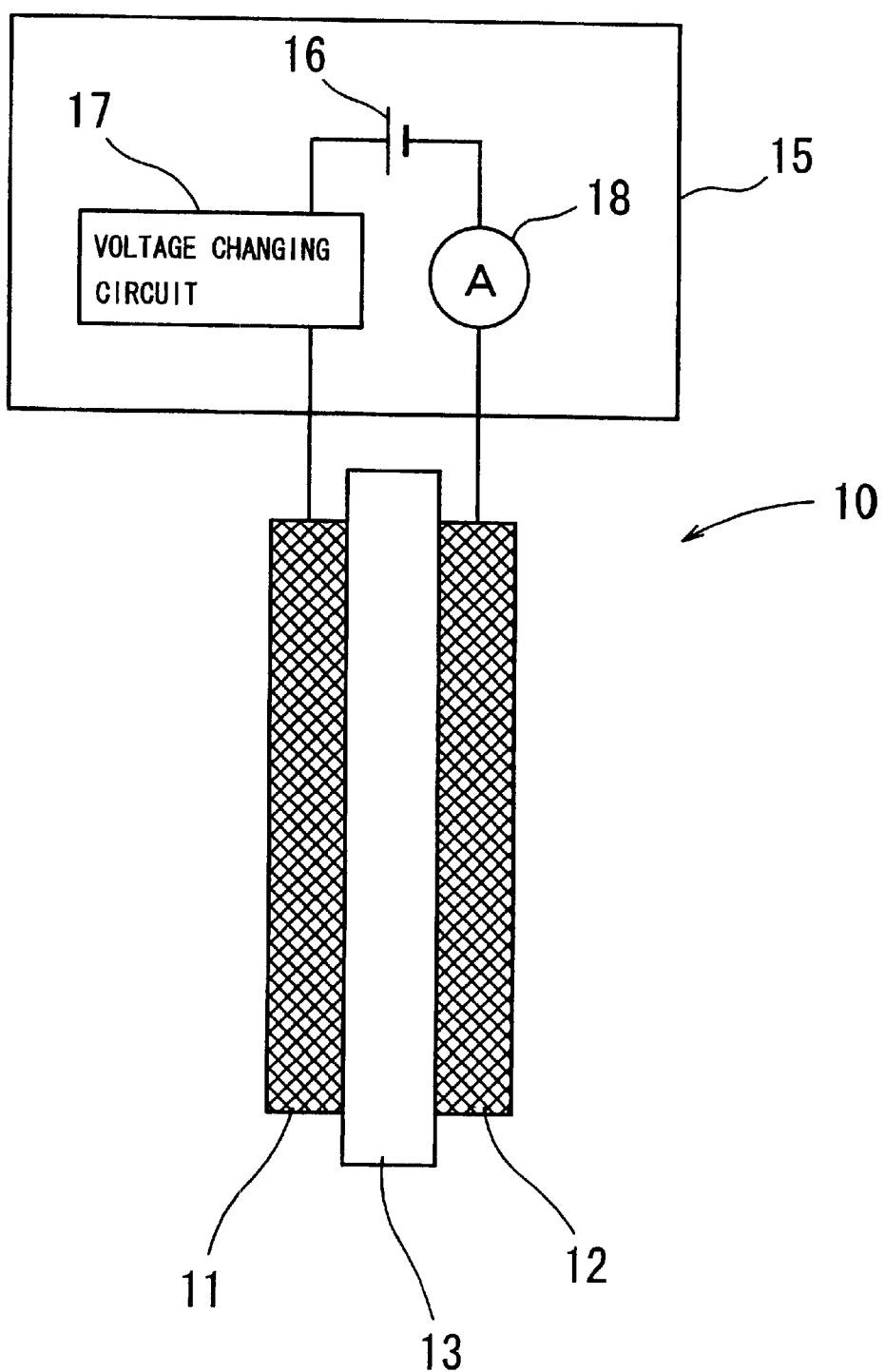
FIG. 4 is a schematic view of one embodiment of the CO gas sensor of the present invention.

FIG. 4 is a diagram of a CO gas sensor 10 according to the present invention, including a sensor control unit 15, a detection electrode 11, a counter electrode 12 and an electrolyte membrane 13. Each component will be explained below.

Detection Electrode 11

The detection electrode 11 is composed of a porous body and a reaction layer. The porous body may be formed of any material which is electrically conductive and electrochemically inactive. An example of such a material electrically conductive carbon. Electrochemically inactive refers to impartation and reception of a charge between CO and hydrogen in a range of voltage applied to a sensor. The body is made porous to provide more surface area per unit volume and to allow a greater amount of a catalyst to be carried on the surface.

The amount of void in the porous body is preferably 10–90%. More preferably, it is 20–60% and, most preferably, 35–45%.

The average void diameter in the porous body is preferably 1 nm–100 μm. More preferably, it is 1 nm–1 μm and, most preferably, 10 nm–0.3 μm.

The reaction layer contains a first catalyst as a first electrochemically active material. Absorption and oxidation of CO and oxidation of $H_2$ take place on the surface of the catalyst over the range of voltage applied to the sensor. Therefore, the catalyst substantially serves as an electrode. A suitable detection electrode is disclosed in WO97/40371 as composed of platinum. The use of the catalyst in the present invention provides a larger electrochemically active area, that is, a larger area in which CO and $H_2$ can be electrochemically adsorbed and oxidized per unit weight. Therefore, the amount of the first catalyst material, which is inherently heavy and expensive, may be reduced.

The first catalyst comprises one or more metals selected from Pt, Au, Cu, Ni, Pd, Ag, Rh, Ru and alloys of one or more said metals. Among them, Pt is preferable.

Fine powders of another material, even if not sold as a catalyst, may be included in the catalyst in the present invention. Any material may be used as long as it provides a larger electrochemically active area per unit weight. CO and $H_2$ are electrochemically adsorbed and oxidized on that active area.

It is preferable that the density of the first catalyst is 1 $ng/cm^2$–10 $mg/cm^2$. When the density of the first catalyst is below 1 $ng/cm^2$, response current is not stable, On the other hand, when the density exceeds 10 $mg/cm^2$, the response current becomes too large. The preferable density of the first catalyst is 10 $ng/cm^2$–1 $mg/cm^2$ and, most preferably, 0.1 $\mu g/cm^2$–10 $\mu g/cm^2$.

The upper limit of the density of the first catalyst is 100 $\mu g/cm^2$. In view of the practicality as a CO sensor, it is preferable that the density be 1 $ng/cm^2$–10 $mg/cm^2$ as described above.

The amount of the first catalyst is important in that it controls the amount of response current flowing through the sensor. In order to improve the sensor's sensitivity to CO gas, its durability and the like, it is preferable that the response current be made small. Therefore, it is desirable to minimize the amount of the first catalyst defining the electrochemically effective electrode area on the detection electrode 11. In the present invention the response current, which flows between the electrodes responsive to application of a voltage equal to the CO adsorption potential, is preferably 0.001 mA/cm2–1 A/cm2, more preferably 0.01 mA/cm2–0.1 A/cm2, and more preferably 0.1 mA/cm2–0.01 A/cm2.

As described above, an amount of the catalyst to be carried is defined by weight of the catalyst per unit area of the porous body, that is, density. Since surface area per unit weight differs for different catalysts, the amount of catalyst is defined as unit surface area of the porous body per specific area of the catalyst and is preferably relative to =1:0.001–100; more preferably, =1:0.01–10; and most preferably, =1:0.1–1.

Thus, as used herein, the specific area is a ratio of a unit area of the porous body to the total surface area of a catalyst carried on the unit area of the porous body.

It is preferable that the thickness of the reaction layer be 0.3 nm–1 cm. When the thickness of the reaction layer is below 0.3 nm, an electrochemically active surface area can not be sufficiently provided even when a catalyst constitutes the reaction layer. When the thickness of the reaction layer exceeds 1 cm, there is the possibility that the test gas will not sufficiently diffuse into the reaction layer. In other words, there is the possibility that the test gas will not rapidly and uniformly diffuse into the reaction layer also as the CO concentration in the test gas changes. More preferably the thickness of the reaction layer is 1 μm–1 mm and, most preferably, 5 μm–10 μm.

The preferred thickness of the reaction layer, i.e., 0.3 nm–15 μm, is a range determined by experimentation. By making the reaction layer of the detection electrode 11 thinner, the effective surface area of the detection electrode 11 (total area of supported catalyst) becomes smaller. From the viewpoint of practicality for use as a CO gas sensor, it is preferable that the thickness of the reaction layer of the detection electrode 11 be 0.3 mm–1 cm, as described above.

Counter Electrode 12

The counter electrode 12 includes a second catalyst as an electrochemically active second material which is supported on an electrically conductive porous body. The porous body may be the same as that for detection electrode. It is preferable that the same porous body be used for both electrodes from the viewpoint of ability to use the same element in different portions of the device.

The second catalyst comprises one or more metals selected from Pt, Au, Cu, Ni, Pd, Ag, Rh, Ru and alloys of one or more of said metals, as in the case of the first catalyst. The catalyst may be wholly dispersed into the body and may be formed into a reaction layer on the body in the same manner as the first catalyst.

Figure 1:
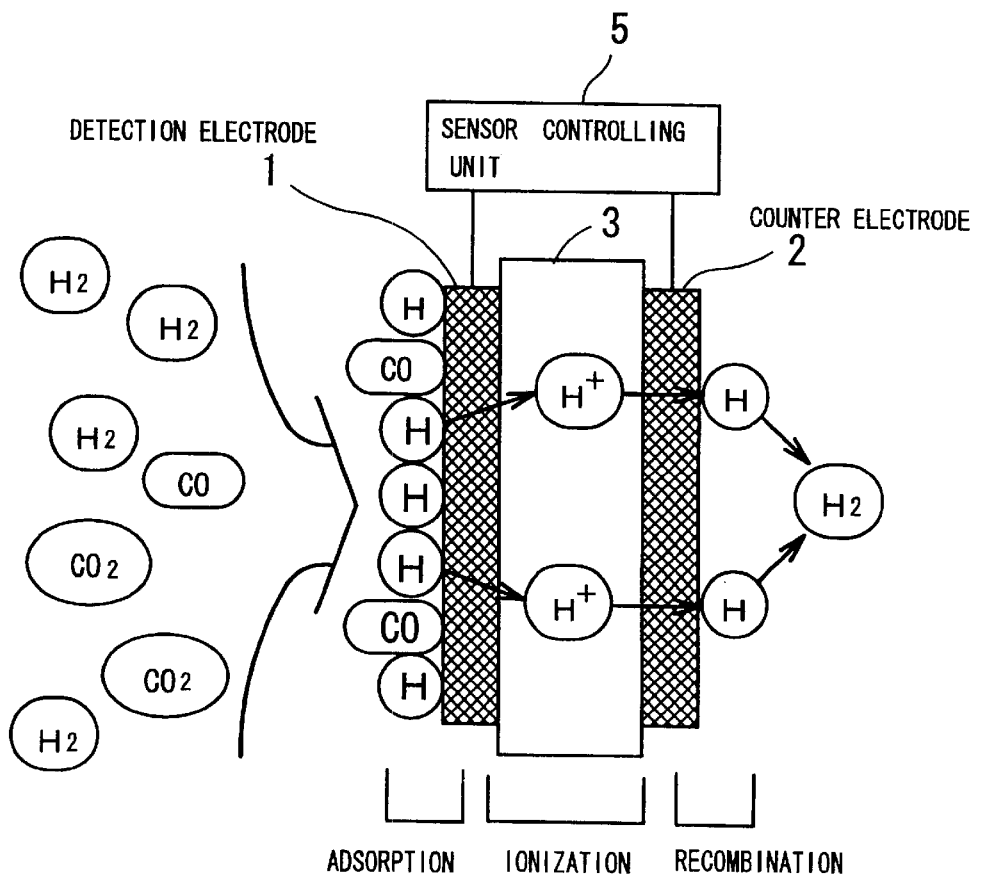
FIG. 1 is a diagram explaining the operating principle of a CO gas sensor.

In use of this second catalyst, a charge is received at and removed from its surface as shown in FIG. 1, i.e., in the manner of the first catalyst of the detection electrode. Accordingly, the second catalyst functions substantially as an electrode. The use of the catalyst in the present invention provides a larger electrochemically active area, that is, an area in which $H^+$ can be electrochemically reduced per smaller volume. Thereby, the amount of the second catalyst, that is inherently heavy and expensive, can be reduced.

It is preferable that the second catalyst of the counter electrode hardly adsorbs CO. This is because when CO is adsorbed onto the counter electrode surface where reduction of hydrogen is effected, the reduction is prevented as shown in FIG. 1. As such second catalyst, a Pt-Ru catalyst can be used.

The amount of the second catalyst to be used can be arbitrarily selected within a range of 1 $ng/cm^2$–10 $mg/cm^2$ according to the study by the present inventors. When the amount of the second catalyst is smaller, there is the possibility that the response current will not be stable. In this invention, the amount of the second catalyst (total amount) is determined by comparison with the amount of the first catalyst (total amount) carried on the detection electrode 11.

According to the study by the present inventors, it is preferable that total weight of the second catalyst such as Pt-Ru and the like carried on the counter electrode 12: total weight of the first catalyst carried on the detection electrode 11 be 0.1–100000:1. More preferably, it is 1–10000:1 and, most preferably, 10–1000:1. This can be also be expressed as a relationship between the electrochemically effective (active) surface area of the counter electrode 12 and the electrochemically effective (active) surface area on the detection electrode 11. That is, assuming that the surface area per unit weight of the catalysts carried on the electrodes is equal, the ratio of the electrochemically effective surface area of the counter electrode 12 to the electrochemically effective surface area of the detection electrode 11 is preferably 0.1–100000:1; more preferably, 1–10000:1; and, most preferably, 10–1000:1.

Electrolyte Membrane 13

The electrolyte membrane 13 is a proton-conducting ion exchange membrane formed of a solid polymer material, for example, fluorinated resin. For example, a Nafion (trade name: Du Pont) membrane and the like can be used. For the electrolyte membrane 13 to allow proton transport, it is necessary to maintain the membrane in a humid state. Therefore, when current flowing through the CO gas sensor 10 increases, the temperature of the sensor rises and the electrolyte membrane 13 may be excessively dried. Accordingly, the humidity in the atmosphere in which the CO gas sensor 10 is placed is also important from the viewpoint of maintaining the moist state of the electrolyte membrane 13.

The membrane thickness of this electrolyte membrane 13 is not particularly limited.

Instead of the electrolyte membrane 13, an electrolysis solution such as aqueous sulfuric acid may be used. In this case, a detection electrode and a counter electrode are immersed in the electrolysis solution.

Figure 5:
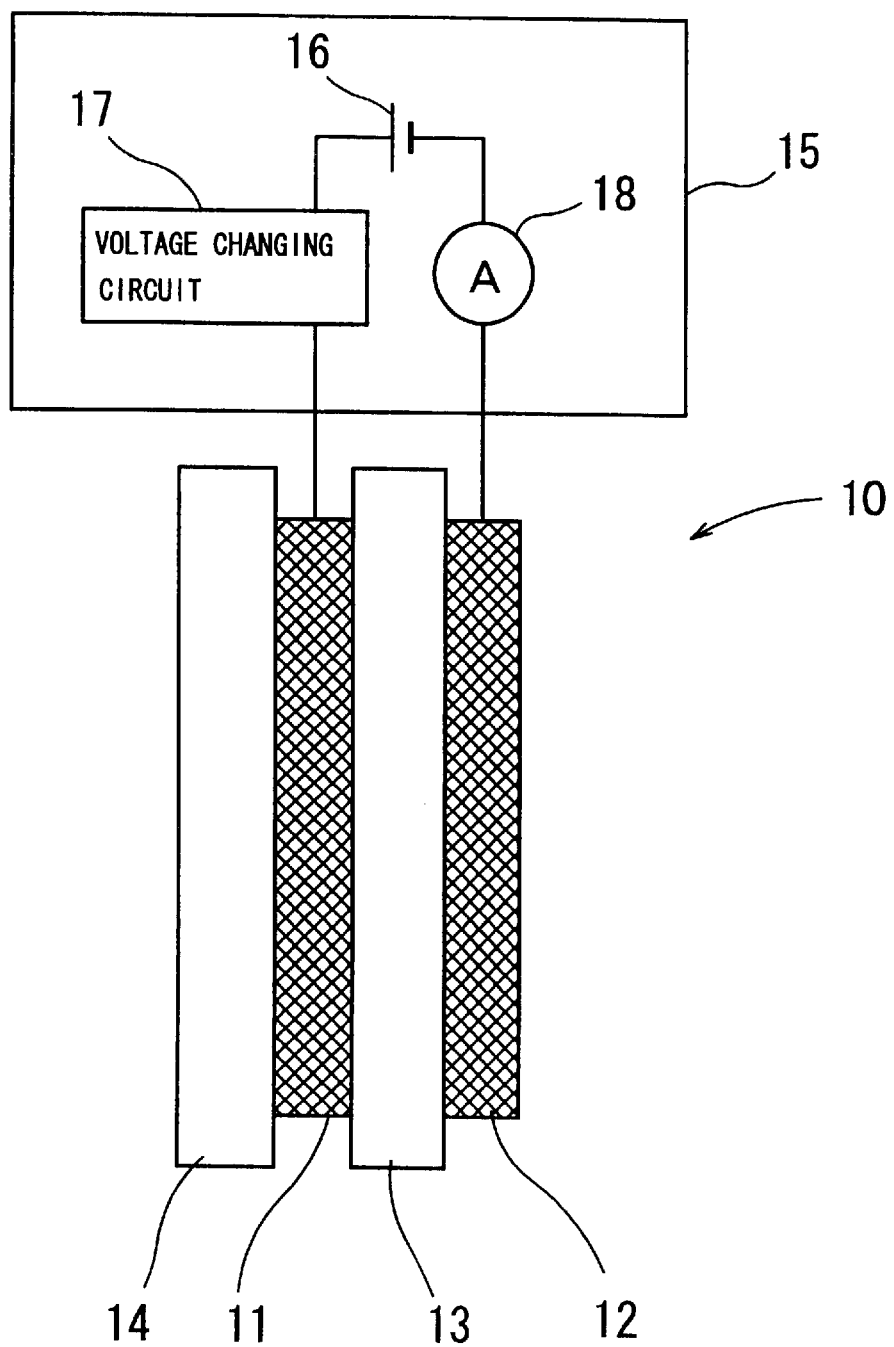
FIG. 5 is a schematic view of a second embodiment of the CO gas sensor of the present invention.

Diffusion Controlling Membrane 14 (see FIG. 5)

As shown in FIG. 5, a diffusion controlling membrane 14 may be disposed on the surface of the detection electrode 11 so as to cover the reaction layer. This diffusion controlling membrane 14 may be a porous membrane (for example, the same porous carbon as that for the porous body) or a liquid membrane (aqueous sulfuric acid) and its membrane thickness is arbitrary.

By provision of the diffusion controlling membrane 14, a detection by the sensor is dependent on and controlled by the gas diffusion rate in the reaction layer formed on the detection electrode 11. When this diffusion controlling membrane 14 is omitted, temperature and humidity affect the Nafion membrane and there is the possibility that the ion conductivity of the membrane will affect the detection by the sensor. Since this invention aims to improve the capability of a sensor by optimizing the reaction layer of the detection electrode as described above, it is preferable that performance of the reaction layer has a direct affect on the performance of the sensor as a whole.

Sensor Controlling Unit 15

Figure 2:
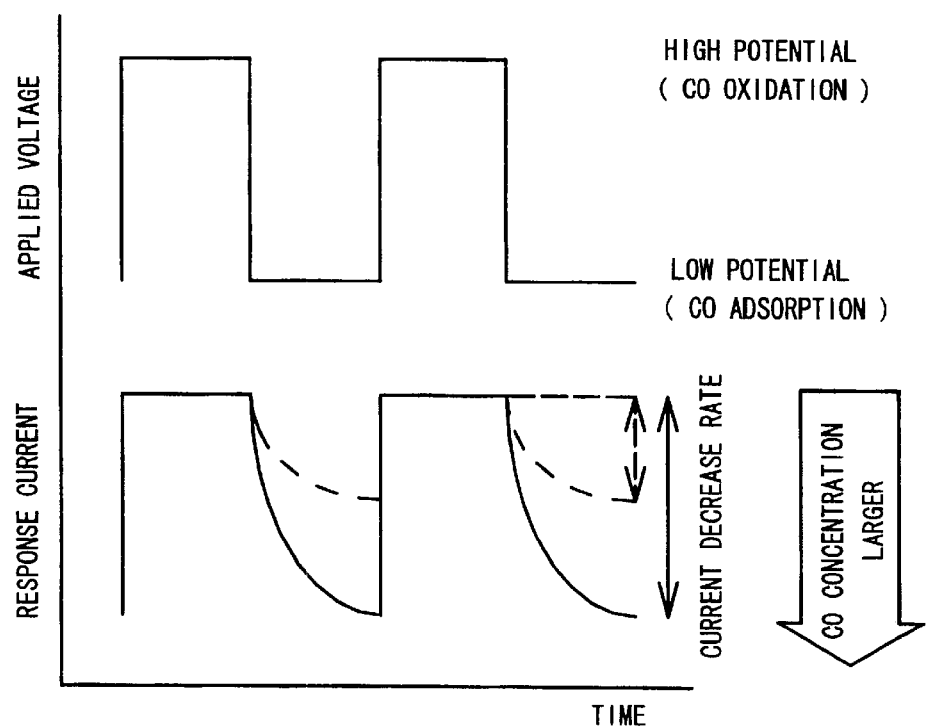
FIG. 2 is a graph showing the relationship between applied voltage and response current in a pulse method.

The sensor controlling unit 15 includes a direct current source 16, a voltage changing circuit 17 and an ampere meter 18. The voltage changing circuit 17 changes voltage of the direct current source 16, for example, into a rectangular wave pulse as shown in the upper portion of FIG. 2. Provided its upper limit is the CO oxidation potential and its lower limit is CO adsorption potential, the pulse wave shape is not particularly limited. The triangle wave and sinusoidal wave shown in WO97/40371 may be adopted. A conventional pulse wave forming circuit may be used in such a voltage changing circuit 17. The ampere meter 18 detects the response current which flows through the sensor when voltage is changed from the CO oxidation potential to the CO adsorption potential.

The CO concentration is obtained by analysis of the thus obtained response current. The analysis may employ: (1) a general purpose calibration curve, (2) a calibration curve developed by Langmuir type CO adsorption, (3) a calibration curve for the relationship between the reciprocal of time for reaching a constant current decrease rate and the CO concentration, (4) a calibration curve for the relationship between an initial current decrease rate and the CO concentration. For details, see WO97/40371.

Of course, a cyclic voltammetry method can also be used. In this case, voltage is swept linearly by a voltage changing circuit 17 through a predetermined range.

Figure 3:
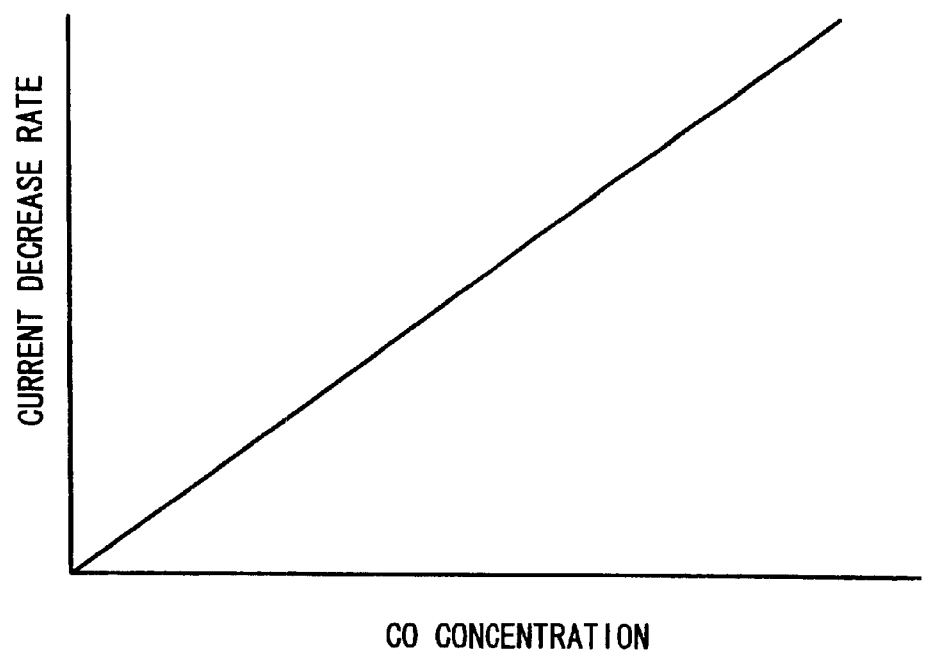
FIG. 3 shows a calibration curve for CO concentration against rate of decrease of response current.
Figure 6:
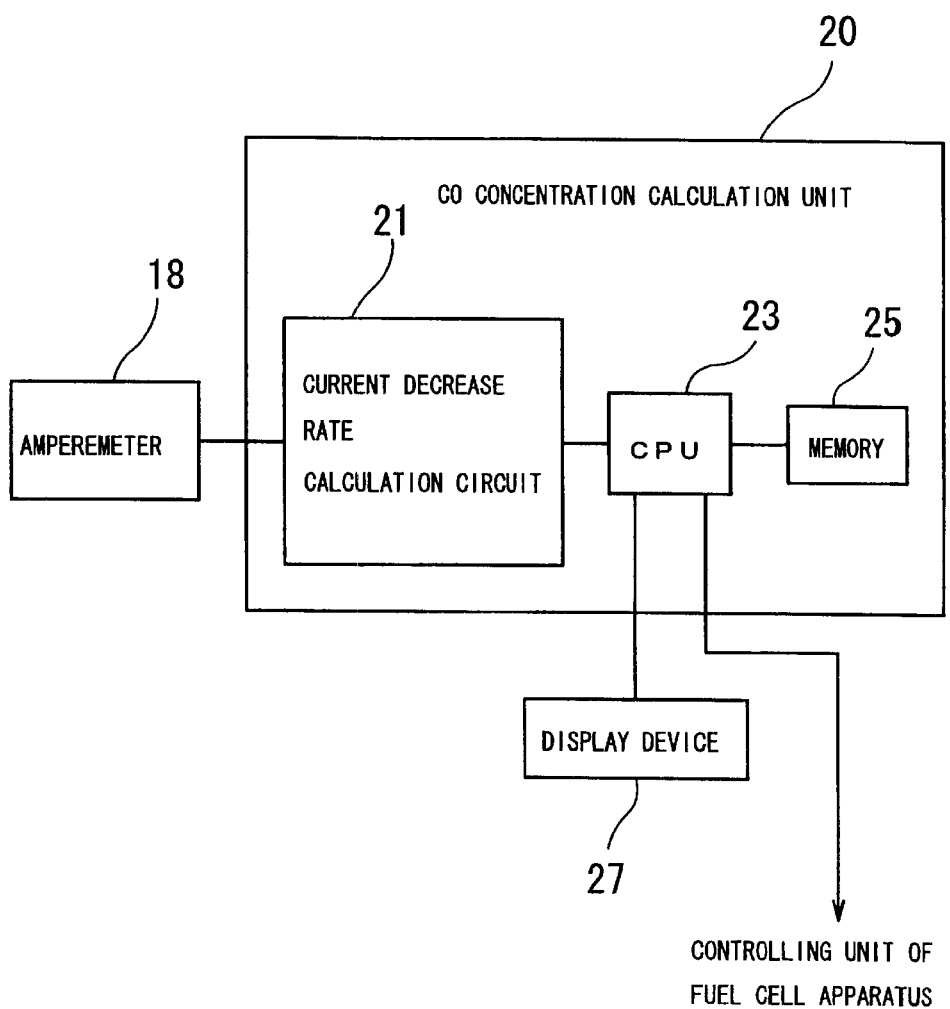
FIG. 6 is a block diagram of a CO concentration operating unit.

A CO concentration calculation unit 20 for determining the CO concentration from the resulting response current is shown in FIG. 6. The CO concentration calculation unit 20 includes a response current decrease rate calculation circuit 21, CPU 23 and a memory 25. The response current decrease rate calculation circuit 21 analyzes the wave shape of the response current detected by the ampere meter 18 and calculates a rate of decrease per predetermined time. A suitable calibration curve, e.g., one of calibration curves (1)–(4), mentioned above, is stored as, for example, a data table format in the memory 25 (see FIG. 3). A control program for controlling the operation of CPU 23 is also stored in the memory 25. The CPU 23 determines the CO concentration from the rate of current decrease calculated by the response current decrease rate calculation circuit 21 by reference to the data table correlating current decrease rate with the CO concentration, which data table is stored in the memory 25. The thus determined CO concentration is displayed on a display device 27 composed of a display, a printer or the like. In addition, when the CO concentration calculation unit 20 is combined with a fuel cell apparatus, the determined CO concentration is sent to a control unit of the fuel cell apparatus.

Figure 7:
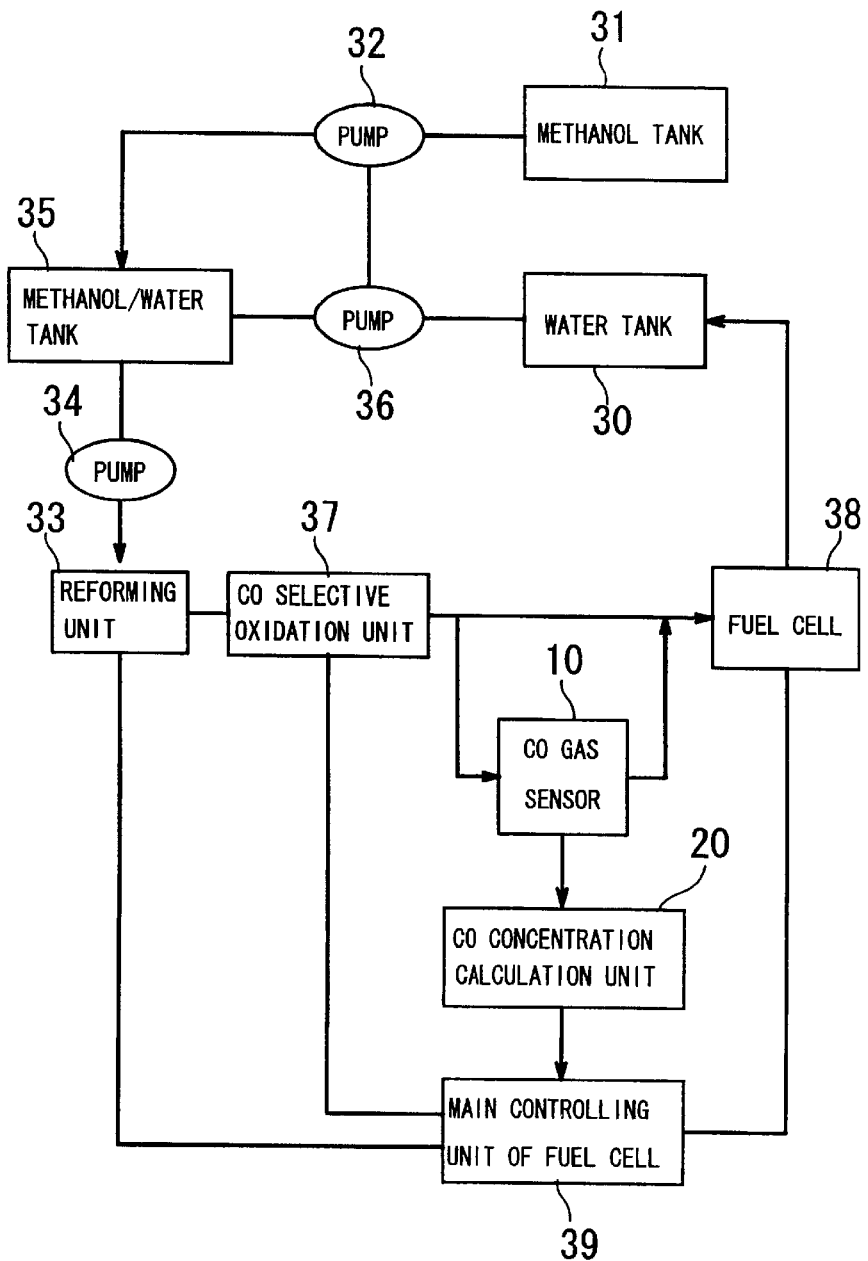
FIG. 7 is a block diagram of a fuel cell apparatus into which a CO gas sensor of the present invention is incorporated.

An example where the CO gas sensor 10 of the present invention is incorporated into a fuel cell apparatus is shown in FIG. 7. In the fuel cell apparatus, methanol is introduced from a methanol tank 31 by a pump 32 and water is introduced from a water tank 30 by a pump 36 into a water/methanol tank 35, and the water/methanol mixture is introduced from the tank 35 into a reforming unit 33 by a pump 34, where it is reformed into a reformed gas ($H_2$: 75%, $CO_2$: 25%, CO: a few hundreds ppm). The reformed gas is supplied to a CO selective oxidation unit 37 and CO in the reformed gas is selectively oxidized and supplied to a fuel cell 38. A part of the fuel gas discharged from the CO selective oxidation unit 37 is supplied to a CO gas sensor 10, where the CO concentration in the fuel gas is measured. The CO concentration is determined by a CO concentration calculation unit 20 based on the response current detected by the CO gas sensor 10. The signal representing CO concentration is supplied to a main control unit 39 of a fuel cell apparatus. The main control unit 39 controls the reaction conditions for CO oxidation in the CO selective oxidation unit 37 based on the detected CO concentration. In addition, when the CO concentration exceeds the predetermined threshold, supply of the fuel gas to the fuel cell 38 is stopped.

The general construction of the CO gas sensor of the example of the present invention and that of the CO gas sensor of the Comparative Example, both of which are described below, is shown in FIG. 4 and the specifications for each are as shown in Table 1. The CO gas sensor which is described below as a Comparative Example is not prior art relative to the present invention.

TABLE 1

| ITEM | | Comparative Ex. | Example |
|---|---|---|---|
| Element | | | |
| Detection Electrode | Catalyst | Pt | ← |
| | Amount | 500 $\mu g/cm^2$ | 0.1–10 $\mu g/cm^2$ |
| | Reaction Layer Thickness | 50–20 $\mu m$ | 10–5 $\mu m$ |
| | Specific Area | 200–100 $cm^2 cm^2$ | 10–0.1 $cm^2 cm^2$ |

TABLE 1-continued

| ITEM | | Comparative Ex. | Example |
|---|---|---|---|
| counter Electrode | Catalyst | Pt | Pt-Ru |
| | Amount | 500 μg/cm² | ← |
| | Reaction Layer Thickness | 50–20 μm | ← |
| | Specific Area | 200–100 cm²cm² | ← |
| Electrolyte Membrane Properties | Material | Nafion | ← |
| | Thickness | 50 μm | ← |
| Response Current | | 1–0.1 A/cm² | 0.01–0.0001 A/cm² |
| Detection Limit | | 20 ppm | 1 ppm |
| Workable Temp. Range | | 70–90° C. | 70–120° C. |
| Workable Hum. Range | | 40–100% RH | 20–100% RH |

In Table 1, a specific area of each electrode is total surface area of catalyst carried on an unit area of a body of each electrode.

In the example of the present invention and the Comparative Example, a Pt catalyst or a Pt-Ru catalyst is coated on the body of each electrode by a conventional method, to form a reaction layer on the surface of the electrode body. Thereafter, a Nafion membrane is placed between the detection electrode and the counter electrode and the whole is hot pressed to form a sensor detecting unit. Each electrode is connected to a sensor controlling unit to obtain the CO sensor shown in FIG. 4.

For purposes of comparison, it is preferable that an amount of the Pt catalyst supported on the detection electrode be 100 μg/cm² or smaller. It is also preferable that the thickness of the detection electrode be 15 μm or smaller. It is preferable that the catalyst supported on the counter electrode is Pt-Ru.

Figure 8:
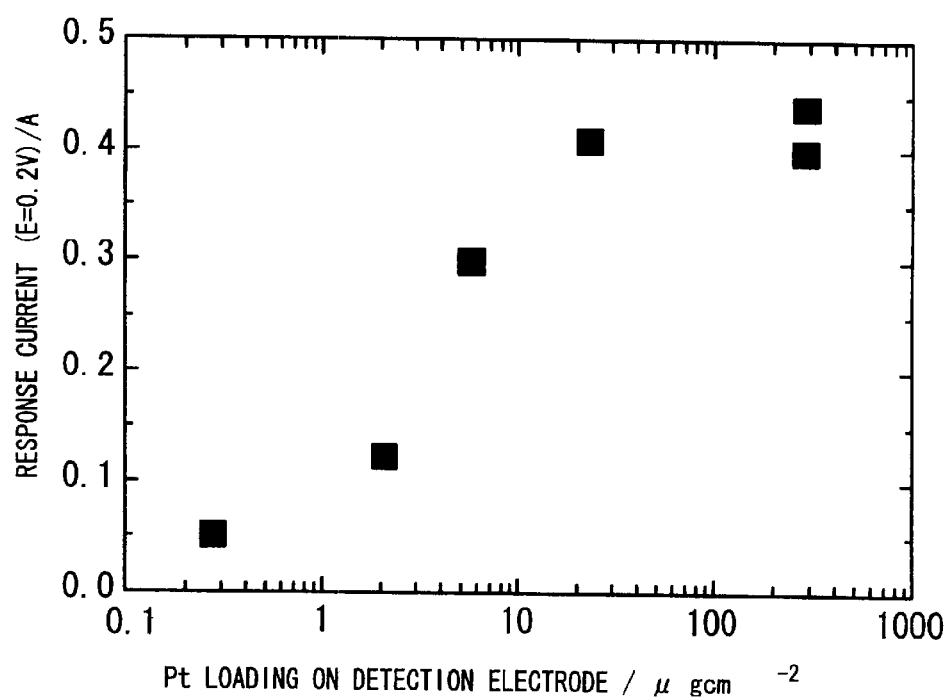
FIG. 8 is a graph showing the relationship between an amount of Pt catalyst and the magnitude of response current in a CO gas sensor of the example representative of the present invention.

FIG. 8 shows the amount of the response current for different amounts of Pt catalyst supported on the detection electrode is varied in the example representative of the present invention. The potential applied to the sensor as a CO adsorption voltage is 0.2 V. From FIG. 8, it is seen that the amount of the Pt catalyst is preferably 100 μg/cm² or smaller. More preferably the amount is 30 μg/cm² or smaller and, most preferably, 1 μg/cm² or smaller.

Figure 9:
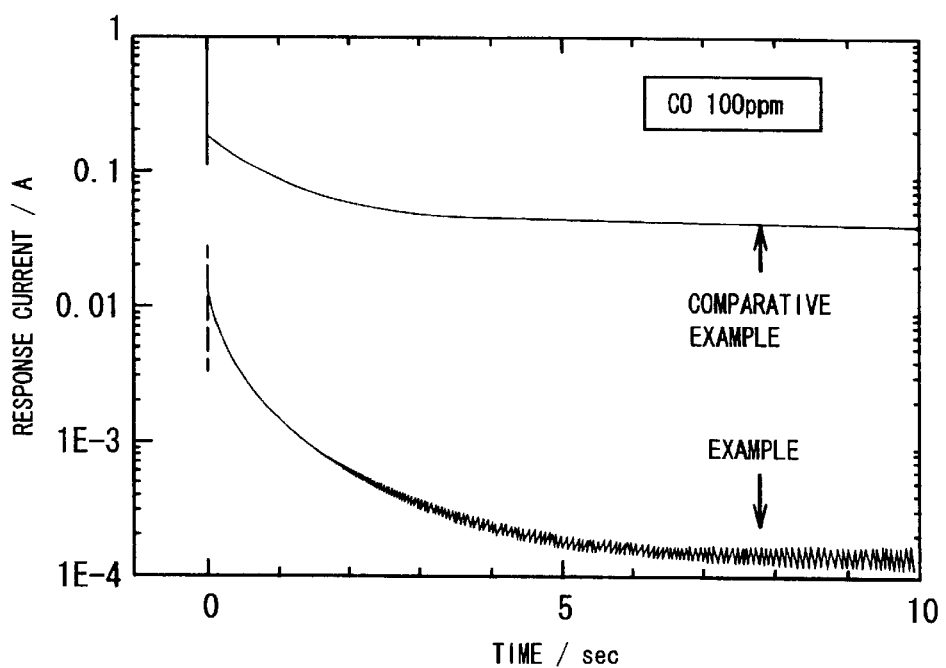
FIG. 9 is a graph presenting a comparison between the magnitude of response current of a CO gas sensor of the Comparative Example and that of a CO gas sensor of the example representative of the present invention.

FIG. 9 shows the profiles of response current in the CO gas sensors of the example of the present invention and the Comparative Example. The data of FIG. 9 was obtained for a CO gas concentration of 100 ppm, a temperature of 90° C., a humidity of 20 mol %, a pressure of 1.5 atm, and a flow rate of 100 liter/min.

As is apparent from FIG. 9, the response current of the CO gas sensor of the example of the invention was 0.1 mA/cm²–0.1 A/cm² and that of the Comparative Example was 1/10–1/1000.

Figure 10A:
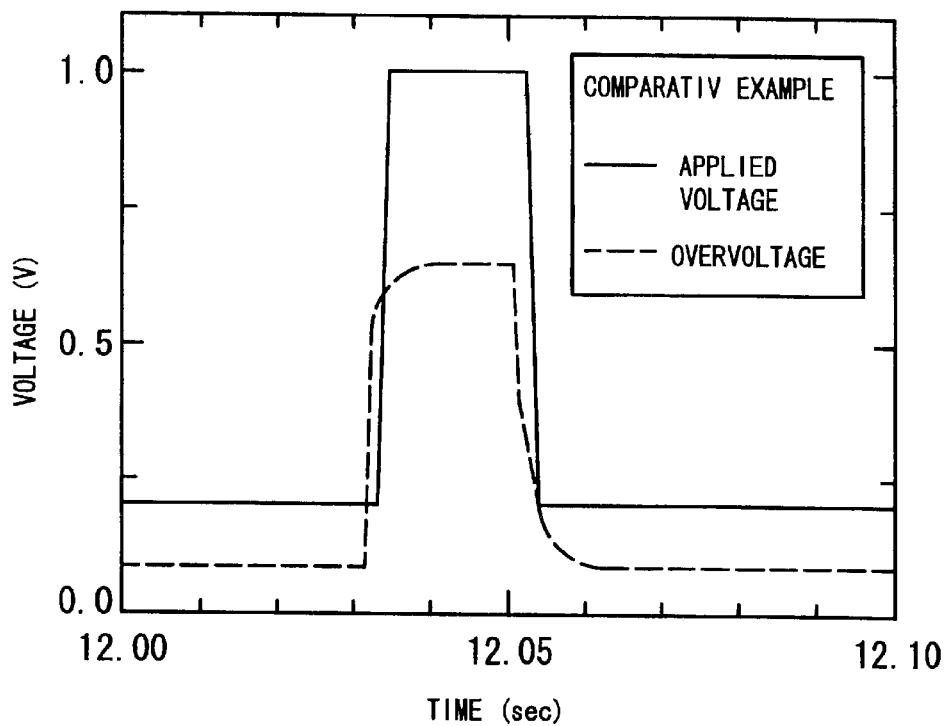
FIG. 10A is a graph of profile of applied voltage and transition voltage in a CO gas sensor in the Comparative Example and FIG. 10B is a graph of applied voltage transition voltage in a CO gas sensor of the example representative of the present invention.
Figure 10B:
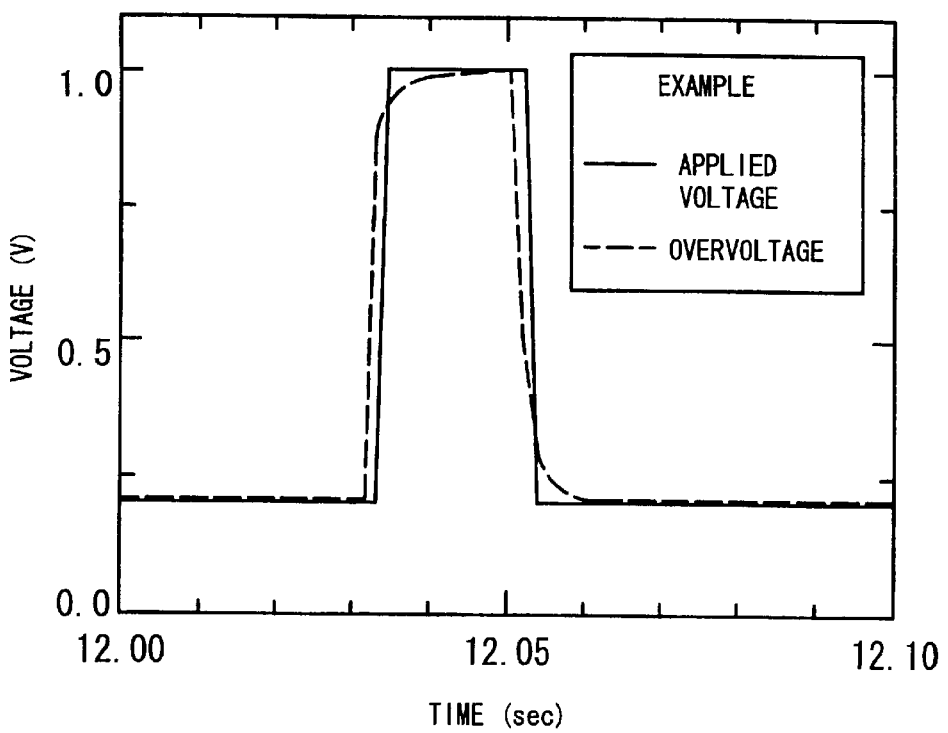

Although A CO gas sensor is considered to have an internal resistance of at least around 1–2Ω, when the intensity of the response current becomes small like this, IR loss becomes nearly zero even when a sensor has such an internal resistance. FIGS. 10A and 10B respectively, show the profile of the applied voltage with the CO gas sensors of the Comparative Example of and the example of the present invention, together with profiles of overvoltage. In the case of the Comparative Example, since the level of response current is high, there is a great difference between the profile of applied voltage and the profile of overvoltage due to IR loss. Because of this difference between profiles, there is the possibility that potential required for CO oxidation and CO adsorption is not as designed. In order to avoid this, a reference electrode was added in the prior art. However, in the case of the example of the present invention, the profile of applied voltage is nearly consistent with that of overvoltage. As a result, potential of the counter electrode is stabilized and it has become possible to omit the reference electrode.

When the IR loss is nulled due to a low current, exotherm becomes nearly zero in the CO gas sensor. For that reason, drying of an electrolyte membrane and its deterioration can be prevented and it becomes possible to extend the life of the CO gas sensor.

Figure 11A:
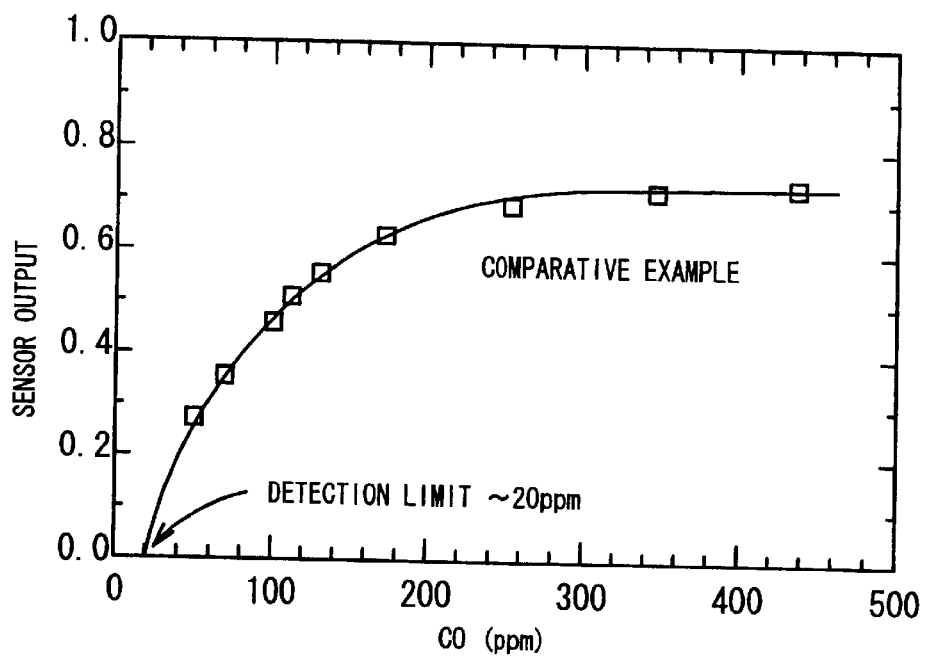
FIG. 11A is a calibration curve showing the sensitivity of a CO gas sensor of the Comparative Example and FIG. 11B is a calibration curve for a CO gas sensor of the example representative of the present invention.
Figure 11B:
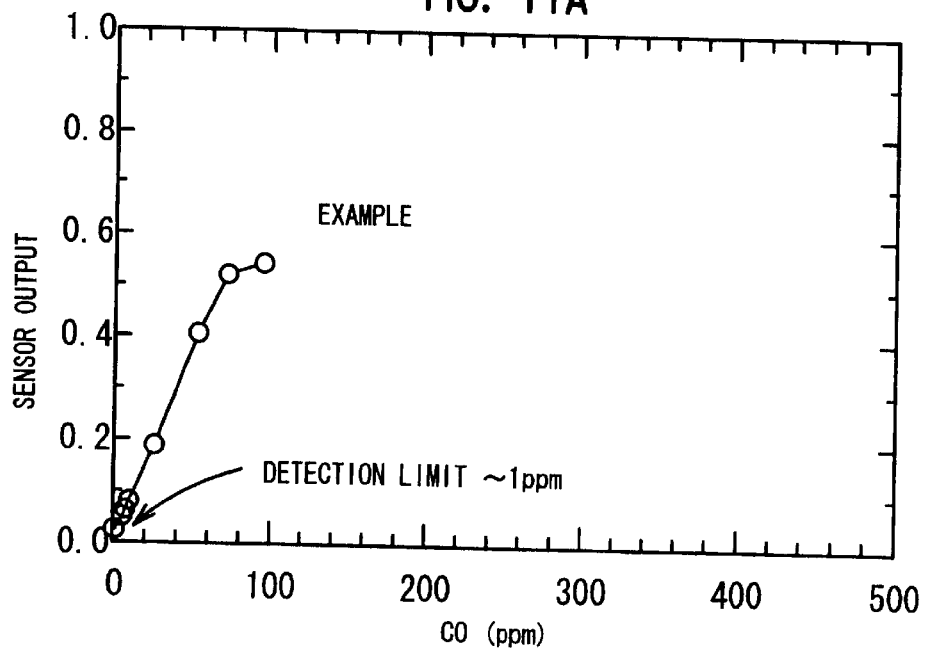

FIGS. 11A and 11B show examples of calibration curves for the CO gas sensors of the Comparative Example and the example of the present invention. As can be seen from the figures, the detection limit for the CO gas sensor of Comparative Example is approximately 20 ppm, while the detection limit of the CO gas sensor of the example of the invention is approximately 1 ppm.

Figure 12:
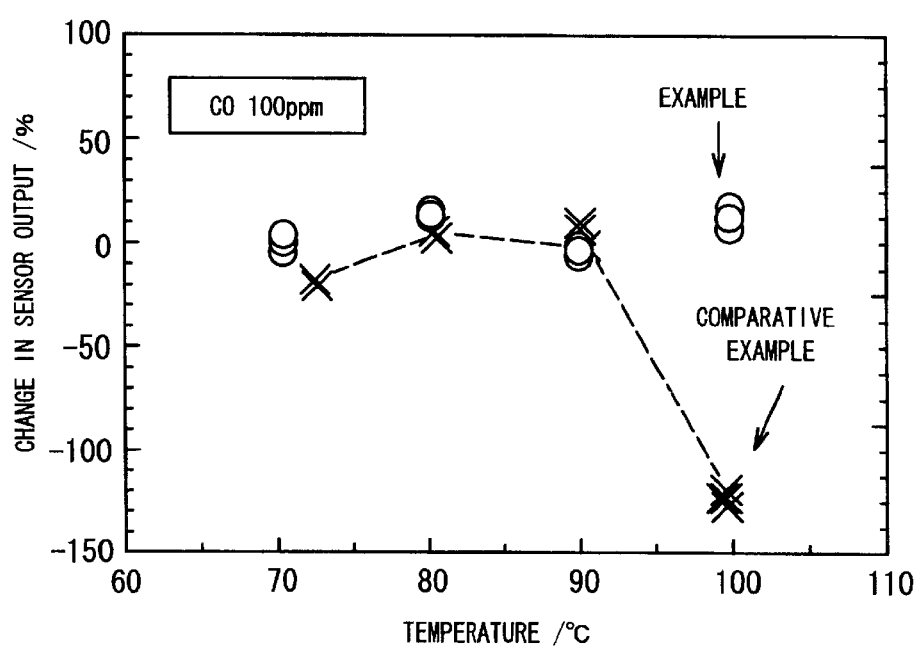
FIG. 12 is a graph showing respective temperature dependencies of the CO gas sensor of the Comparative Example and that of the example representative of the present invention.

FIG. 12 shows temperature dependency for both of the CO gas sensor of the Comparative Example and the CO gas sensor of the example of the invention. As apparent from the figures, the CO gas sensor of the Comparative Example does not endure high temperature as well as that of the example of the invention because of decrease in sensor output when temperature exceeds 90° C. On the other hand, in the CO gas sensor of the example of the invention, sensor output is stable up to 100° C.

In FIG. 12, sensor output change (%) (the ordinate) is obtained by expressing the response current decrease rate responsive to an initially applied rectangular pulse at each temperature using a decrease rate at 90° C. as a standard (100%). The conditions under which the data of FIG. 12 was obtained were CO concentration: 100 ppm; humidity: 20 mol %, pressure: 1.5 atm; and flow rate: 100 liter/min.

Figure 13:
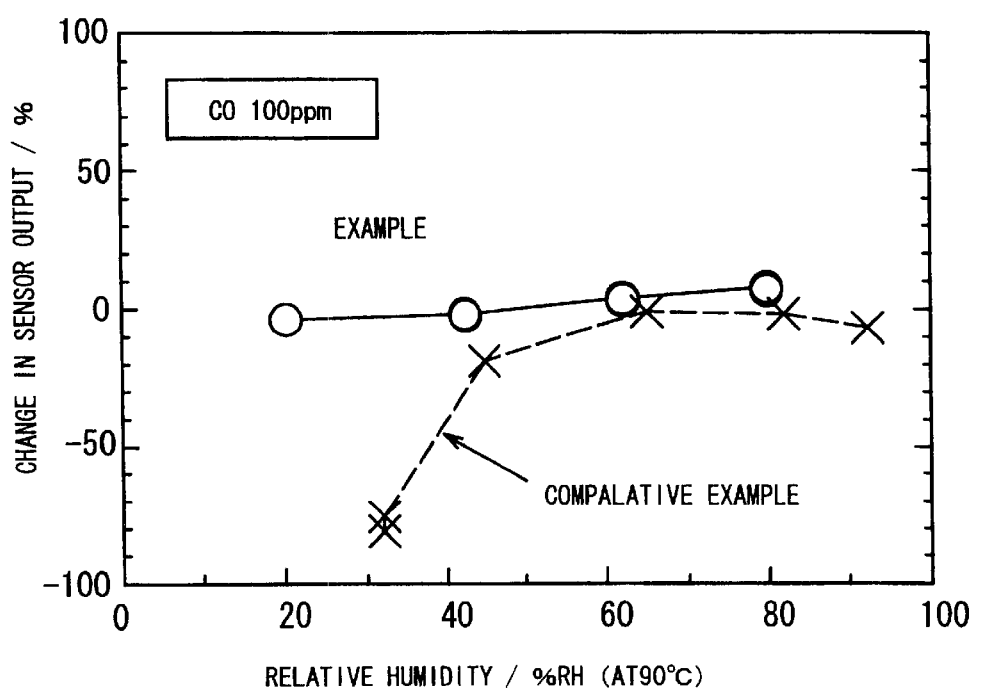
FIG. 13 is a graph showing respective humidity dependencies of a CO gas sensor of the Comparative Example and a CO gas sensor of the example representative of the present invention.

FIG. 13 shows the humidity dependency of the CO gas sensor of Comparative Example and that of the CO gas sensor of the example of the present invention. As is apparent from the figure, the CO gas sensor of Comparative Example does not endure when the humidity falls below 40% RH. On the other hand, the CO gas sensor of the example of the invention is stable in sensor output up to 20% RH.

In FIG. 13, sensor output change (%) (the ordinate) is obtained by expressing response current decrease rate when rectangular pulse is applied initially at each temperature using a decrease rate at 65% RH as a standard (100%). The conditions under which the data of FIG. 13 was obtained were CO concentration: 100 ppm, temperature: 90° C., pressure: 1.5 atm and flow rate: 100 liter/min.

It is believed that the temperature range and range of humidity are affected by one or more of the following factors: (1) reduction in response current, (2) the thickness of the detection electrode, and (3) selection of the metal catalyst for the counter electrode.

The present invention is not limited to the above embodiments of the invention nor to the explanation of the example. A variety of embodiments may be included in the present invention without departing from the scope of the claims, as is obvious to a person skilled in the art.

What is claimed is:

1. A CO gas sensor for measuring CO concentration in an atmosphere containing CO and hydrogen gases, said sensor comprising:
    a detector including a detection electrode, a counter electrode and a solid electrolyte member sandwiched between said detection electrode and said counter electrode, wherein said detection electrode comprises a first electrochemically active catalyst carried on an electrically conductive porous body and forming a reaction layer thereon, said first catalyst having a density of 1 ng/cm$^2$–100 μg/cm$^2$ and a thickness of 0.3 nm–15 μm, and wherein said counter electrode comprises a second electrochemically active catalyst carried on an electrically conductive porous body;

means for contacting said detector with the atmosphere;

voltage application means for applying, between said detection electrode and said counter electrode while in contact with the atmosphere, a voltage in a wave form wherein the voltage continuously cycles between CO oxidation potential and CO adsorption potential and for thereby causing a response current to flow between said electrodes responsive to the applied voltage;

means for measuring the amount of response current; and determination means for determining the CO concentration based on the measured amount of response current.

2. The CO gas sensor according to claim 1, wherein the first catalyst and the second catalyst are each a metal selected from the group consisting of Pt, Au, Cu, Ni, Pd, Ag, Rh, Ru and alloys of said metals.

3. The CO gas sensor according to claim 1, wherein the first catalyst comprises Pt and the second catalyst comprises Pt-Ru.

4. The CO gas sensor according to claim 1, wherein a second reaction layer comprising the second catalyst is formed on the porous body of the counter electrode and a total weight of the second catalyst in the second reaction layer is 10–1000-fold of total weight of the first catalyst in the reaction layer of the detection electrode.

5. The CO gas sensor according to claim 1, wherein said counter electrode has an electrochemically active area 10–1000-fold of an electrochemically active area of the detection electrode.

6. The CO gas sensor according to claim 1, wherein the body of the detection electrode has a void rate of 10–90% and an average void diameter of 1 nm–100 μm.

7. The CO gas sensor according to claim 1, further comprising a diffusion controlling membrane disposed on the detection electrode.

8. A fuel cell apparatus equipped with the CO gas sensor according to claim 1.

9. The CO gas sensor according to claim 1 wherein said determination means determines the CO concentration based on rate of decrease in the measured amount of response current.

10. The CO gas sensor according to claim 1 wherein said voltage application means comprises a direct current voltage source and a voltage changing circuit.

11. A CO gas sensor for measuring CO concentration in an atmosphere containing CO and hydrogen gases, said sensor comprising:

a detector including a detection electrode, a counter electrode and a solid electrolyte member sandwiched between said detection electrode and said counter electrode;

means for contacting said detector with the atmosphere;

voltage application means for applying, between said detection electrode and said counter electrode while in contact with the atmosphere, a voltage in a wave form wherein the voltage continuously cycles between CO oxidation potential and CO adsorption potential and for thereby causing a response current to flow between said electrodes responsive to the applied voltage, said response current being 0.001 mA/cm$^2$ to 1 A/cm$^2$ at said CO adsorption potential;

means for measuring the amount of response current; and determination means for determining the CO concentration based on the measured amount of response current.

12. The CO gas sensor according to claim 11, wherein said response current is 0.01 mA/cm$^2$–0.1 A/cm$^2$ at the CO adsorption potential.

13. The CO gas sensor according to claim 11, wherein said response current is 0.1 mA/cm$^2$–0.01 A/cm$^2$ at the CO adsorption potential.

14. A fuel cell apparatus equipped with the CO gas sensor according to claim 11.

15. The CO gas sensor according to claim 11 wherein said determination means determines the CO concentration based on rate of decrease in the measured amount of response current.

16. The CO gas sensor according to claim 11 wherein said voltage application means comprises a direct current voltage source and a voltage changing circuit.

17. A CO gas sensor for measuring CO concentration in an atmosphere containing CO and hydrogen gases, said sensor comprising:

a detector including a detection electrode, a counter electrode and a solid electrolyte member sandwiched between said detection electrode and said counter electrode, wherein the detection electrode comprises a porous body which is electrochemically inactive and has electrical conductivity, and a reaction layer which is formed on the body and contains an electrochemically active first material, wherein density of the reaction layer is 1 ng/cm$^2$–100 μg/cm$^2$ and thickness of the reaction layer is 0.3 nm–15 μm;

means for contacting said detector with the atmosphere;

voltage application means for applying, between said detection electrode and said counter electrode while in contact with the atmosphere, a voltage in a wave form wherein the voltage continuously cycles between CO oxidation potential and CO adsorption potential and for thereby causing a response current to flow between said electrodes responsive to the applied voltage;

means for measuring the amount of response current; and determination means for determining the CO concentration based on the measured amount of response current.

18. A method for measuring CO concentration in an atmosphere containing CO and hydrogen gases, said method comprising:

providing a detector including a detection electrode, a counter electrode and a solid electrolyte membrane sandwiched between said detection electrode and said counter electrode;

contacting the detector with the atmosphere;

applying a voltage between said electrodes while in contact with the atmosphere, said voltage continuously alternating between a CO oxidation potential upper limit and a CO adsorption potential lower limit, thereby causing a response current to flow between the electrodes responsive to the applied voltage;

determining the rate of current decrease in transition from the CO oxidation potential to the CO adsorption potential; and determining CO concentration based on the determined rate of current decrease.

* * * * *